(12) United States Patent
Landgraf et al.

(10) Patent No.: US 10,945,624 B2
(45) Date of Patent: Mar. 16, 2021

(54) WIRELESS CARDIAC SENSOR

(71) Applicant: Eko Devices, Inc., Berkeley, CA (US)

(72) Inventors: Connor Landgraf, San Francisco, CA (US); Philip Goolkasian, San Francisco, CA (US); Tyler Crouch, San Francisco, CA (US)

(73) Assignee: EKO DEVICES, INC., Berkeley, CA (US)

( * ) Notice: Subject to any disclaimer, the term of this patent is extended or adjusted under 35 U.S.C. 154(b) by 0 days.

(21) Appl. No.: 15/455,987

(22) Filed: Mar. 10, 2017

(65) Prior Publication Data
US 2018/0256061 A1    Sep. 13, 2018

(51) Int. Cl.
*A61B 5/0408* (2006.01)
*A61B 5/00* (2006.01)
*A61B 7/04* (2006.01)
*A61B 5/024* (2006.01)

(52) U.S. Cl.
CPC ........ *A61B 5/04085* (2013.01); *A61B 5/0006* (2013.01); *A61B 5/6898* (2013.01); *A61B 7/04* (2013.01); *A61B 5/024* (2013.01); *A61B 2562/16* (2013.01)

(58) Field of Classification Search
CPC .............. A61B 5/0404; A61B 5/04845; A61B 5/04085; A61B 5/0006; A61B 7/04; A61B 2562/16

See application file for complete search history.

(56) References Cited

U.S. PATENT DOCUMENTS

| 6,409,675 | B1 * | 6/2002 | Turcott | A61B 5/0002 600/504 |
| 8,855,757 | B2 | 10/2014 | Kapoor | |
| 2004/0032957 | A1 * | 2/2004 | Mansy | A61B 5/04085 381/67 |
| 2005/0014999 | A1 * | 1/2005 | Rahe-Meyer | A61B 5/01 600/323 |

(Continued)

OTHER PUBLICATIONS

Dan, Chunmei et al., "Playing and Acquiring Heart Sounds and Electrocardiogram Simultaneously Based on LabVIEW", 2008 World Automation Congress, Hawaii, HI, 2008, pp. 1-4 (http://ieeexplore.ieee.org/stamp/stampjsp?tp=&arnumber=4699304&isnumber=4698939).

(Continued)

*Primary Examiner* — George R Evanisko
(74) *Attorney, Agent, or Firm* — McCoy Russell LLP

(57) ABSTRACT

A wireless cardiac sensor is provided. The sensor may be utilized by a patient, on themselves, in an at home or other non-clinical environment. A sensor housing contains ECG electrodes and an audio transducer to simultaneously capture heart sound and ECG data with a single device. The ECG electrodes may be positioned on opposite sides of, and preferably adjacent to, an audio transducer sensor, for placement against a user's chest. The wireless cardiac sensor may include a button on a surface opposite the ECG electrodes and audio sensor, facilitating one-handed operation by a patient. The sensor transmits acquired data to a personal electronic device, such as a smartphone, via a wireless communication link. The personal electronic device may in turn transmit data to a centralized server and/or health care provider devices, via a wide area network.

13 Claims, 7 Drawing Sheets

(56) References Cited

U.S. PATENT DOCUMENTS

| | | | |
|---|---|---|---|
| 2005/0078533 A1 | 4/2005 | Vyshedskiy et al. | |
| 2006/0047215 A1* | 3/2006 | Newman | A61B 5/0002 |
| | | | 600/513 |
| 2007/0208233 A1 | 9/2007 | Kovacs | |
| 2013/0116584 A1* | 5/2013 | Kapoor | A61B 5/02 |
| | | | 600/513 |
| 2014/0328210 A1 | 11/2014 | Knaappila | |
| 2015/0057512 A1 | 2/2015 | Kapoor | |
| 2015/0065814 A1 | 3/2015 | Kapoor | |
| 2015/0327775 A1* | 11/2015 | Carter | A61B 7/04 |
| | | | 600/301 |
| 2016/0014550 A1 | 1/2016 | Chiddarwar et al. | |
| 2016/0100817 A1 | 4/2016 | Hussain | |
| 2016/0144192 A1 | 5/2016 | Sanghera et al. | |
| 2018/0168473 A1* | 6/2018 | Du | A61B 5/04085 |

OTHER PUBLICATIONS

PCT International Search Report, International application No. PCT/US17/67337 (dated Jan. 30, 2018).

PCT Written Opinion of the International Searching Authority, International Application No. PCT/US17/67337 (dated Jan. 30, 2018).

PR Newswire. Smart Heart Monitor Keeps the Cardiologist a Heartbeat Away. MPO. (Jun. 7, 2017) retrieved from https://www.mpo-mag.com/contents/view_breaking-news/2017-06-07/smart-heart-monitor-keeps-the-cardiologist-a-heartbeat-away.

PCT International Search Report, International application No. PCT/US18/021964 (dated May 30, 2018).

Rijuven Corp., "i2Dtx CardioSleeve", downloaded from http://rijuven.com/medicaldevices/cardiosleeve on Mar. 5, 2017.

\* cited by examiner

WIRELESS CARDIAC SENSOR

TECHNICAL FIELD

The present disclosure relates to medical devices utilizing wireless electronic communications. More specifically, this disclosure relates to wireless mobile cardiac sensors and uses thereof.

BACKGROUND

As healthcare costs continue to escalate, solutions to reduce the cost and improve the efficacy of diagnostic efforts become increasingly important. In other situations, improving access to medical diagnostic and monitoring capabilities may be desirable. These objectives may be particularly valuable for cardiac care, since cardiac function is vital to human health and well-being, and cardiovascular diseases continue to be the most common cause of death.

However, traditional cardiac monitoring and evaluation tools are not well-suited to non-clinical environments. Equipment may be costly and difficult to use for untrained lay users. Cardiac monitoring equipment often involves numerous sensors, requiring specific placement, which may be difficult and time consuming for lay users to apply, and particularly difficult for a user to apply to themselves—thereby preventing or discouraging regular use. Sensor cables can become tangled, pulled and damaged, further frustrating users and reducing equipment reliability. In addition, the majority of all cardiac monitors currently providing continuous monitoring are limited to a short period of time, typically 2 weeks or 30 days. This time limitation is very significant because many cardiac conditions manifest themselves over a long period of months or years, where a short continuous monitoring window will not be useful for the lifetime of the disease. In view of these and other issues, traditional cardiac monitoring equipment may be particularly unsatisfactory for use by patients at their homes, or in other non-clinical environments.

SUMMARY

A wireless cardiac sensor is provided. In some embodiments, the sensor may be effectively used by lay users in an at home or other non-clinical environment. The sensor includes an audio transducer and ECG electrodes to simultaneously capture heart sound and ECG data. The audio transducer includes a sensor that, together with ECG transducer electrodes, may be positioned on a front surface of a wireless cardiac sensor housing. In some embodiments, ECG electrodes may be arranged on opposite sides of, and preferably adjacent to, the audio transducer sensor.

A button may be provided for user interaction with the wireless cardiac sensor. The button may be used for initiating a cardiac monitoring function. The button may be positioned on a back surface of the wireless cardiac sensor, preferably opposite the audio transducer sensor and ECG electrodes, such that the application of pressure on the button may operate to improve contact with the user's body when in use. Thus, in some applications, the wireless cardiac sensor may be applied to a user's own body, with one hand.

The wireless cardiac sensor may also include a wireless transceiver, for transmitting measured cardiac data to a separate personal electronic device, such as a smartphone, tablet computer, or personal computer. In some embodiments, the wireless cardiac sensor includes a Bluetooth transceiver, for exchanging data with a personal electronic device via a Bluetooth communications link. The personal electronic device includes user interface components, such as a display screen. The personal electronic device display screen may present instructions for proper sensor placement to the user. The personal electronic device may process cardiac data received from the wireless cardiac sensor, and display diagnostic information derived therefore. Data from the wireless cardiac sensor may be stored locally within the personal electronic device, and/or transmitted to remote computing systems for storage and/or analysis.

DETAILED DESCRIPTION OF THE DRAWINGS

Figure 1:
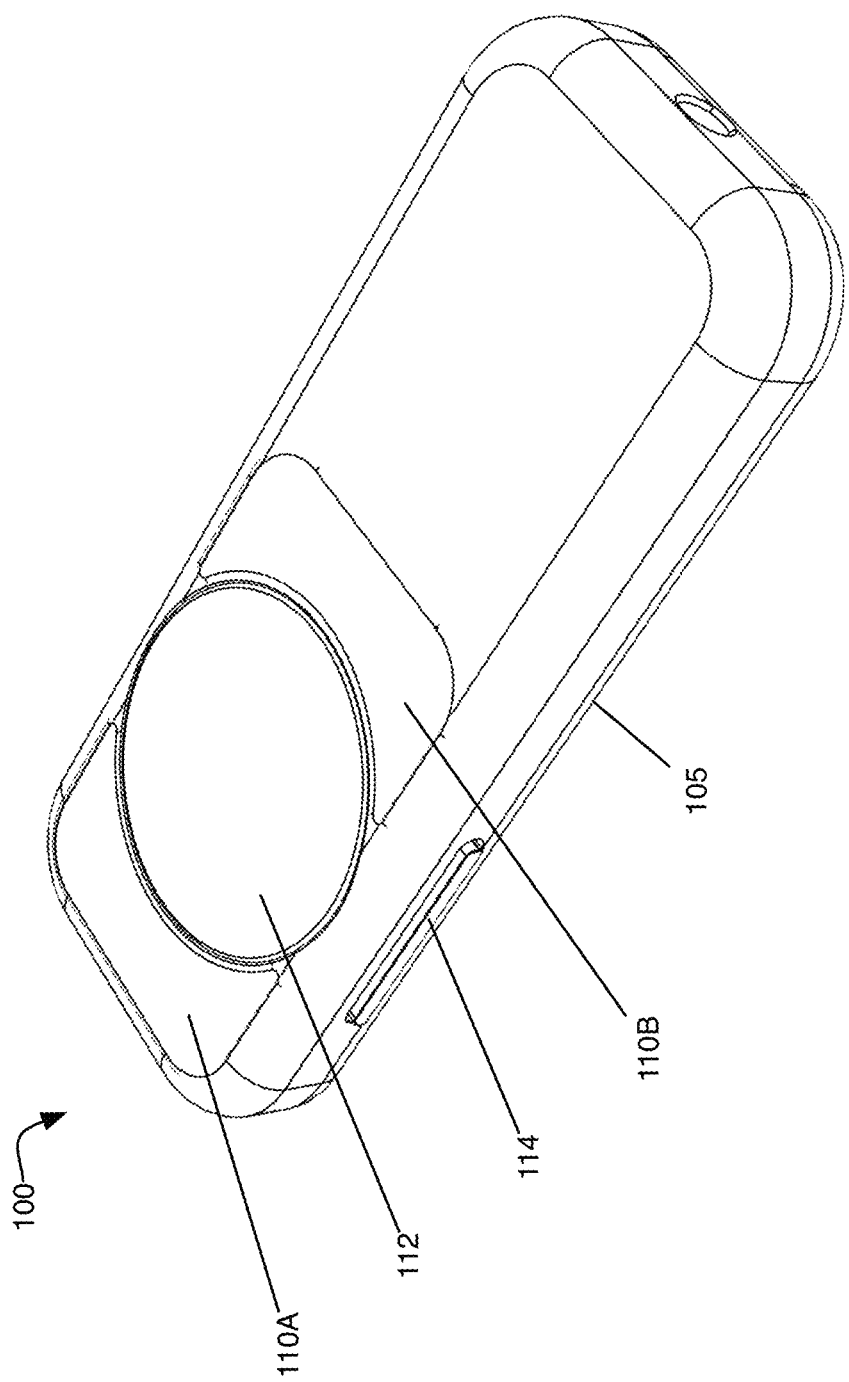
FIG. 1 is a front perspective view of a wireless cardiac sensor, in accordance with one embodiment.

While this invention is susceptible to embodiment in many different forms, there are shown in the drawings and will be described in detail herein several specific embodiments, with the understanding that the present disclosure is to be considered as an exemplification of the principles of the invention to enable any person skilled in the art to make and use the invention, and is not intended to limit the invention to the embodiments illustrated.

In accordance with some embodiments, a portable cardiac transducer may be provided that is portable, cost-effective, and simple-to-use for layperson and self-diagnostic applications.

FIG. 1 is a front perspective view of a wireless cardiac sensor 100. Housing 105 encases circuitry described further hereinbelow, and is preferably formed from plastic or other non-conductive material. Housing 105 is generally rectangular cuboid in shape, with rounded edges. Sensor 100 further includes ECG transducer electrodes 110A and 110B, positioned on a front side of housing 105. Electrodes 110A and 110B are physically separated from one another to facilitate measurement of electrical signals on a person's skin resulting from depolarization of the person's heart muscle during each heartbeat, when appropriately positioned, e.g., against a user's chest on the user's left pectoral region.

Figure 4:
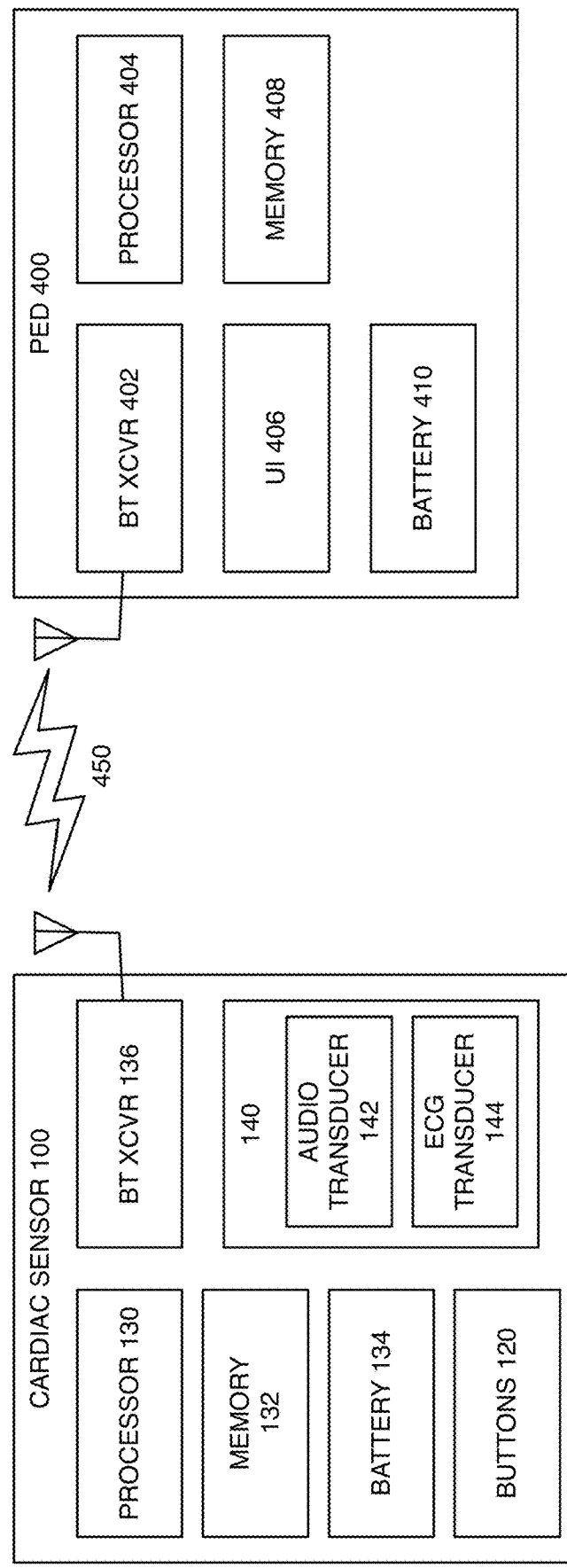
FIG. 4 is a schematic block diagram of a wireless cardiac sensor and a personal electronic device, communicating via a wireless communication channel.

In the embodiment of FIG. 1, electrodes 110A and 110B are positioned adjacent to, and on opposite sides of, acoustic sensor 112, which is also positioned on the front side of transducer 100. When placed against a user's chest, acoustic sensor 112 may be utilized to detect, record and/or characterize a user's heart sounds, as conducted acoustically through their chest wall. Acoustic sensor 112 may be a piezoelectric sensor, which along with associated analog-todigital converters and signal processing components, forms audio transducer 142 (FIG. 4). Collectively, ECG electrodes 110A and 110B and acoustic sensor 112 form a sensor package occupying a portion of the front side of sensor housing 105.

By providing an integrated ECG and heart sound sensor within a unitary housing communicating with a wireless communication protocol, cardiac sensor 100 provides significant usability and reliability benefits, particularly for layperson users and/or users of the cardiac sensor in home, field and other non-clinical environments. For example, combining ECG and heart sound sensors in a unitary package allows an individual to easily use the device on themselves, using one hand. Combining ECG and heart sound sensors in one package allows for precise examination of the electrical and mechanical characteristics of the heart. Positioning electrodes 110 and sensor 112 proximate one another, and preferably adjacent, provides a unitary sensor package for a user to position on their chest. The absence of lead wires prevents users from become entangled in wires. The absence of lead wires also improves reliability, as kinked, pulled or tangled cords and strained connectors are common points of failure for conventional cardiac sensors.

The shape and design of the sensor housing is optimized to balance multiple factors, including (1) comfort for a user to securely hold against their own chest (fits in the hand); (2) secure fit against a wide variety of patient body types and shapes, male and female, for good contact with electrodes 110A/B and acoustic sensor 112; (3) providing sufficient physical separation of the two ECG electrodes to provide accurate signal quality; and (4) providing an audio transducer sensor of sufficient diameter for optimal detection of heart and lung sound frequencies. The ECG electrodes are of a sufficient size to allow good electrical contact between the patient's skin and the electrode even if the patient has chest hair or curves of their skin. The ECG electrodes are of a set separation distance to allow for precision placement over the iso-electric lines of the heart.

Figure 2:
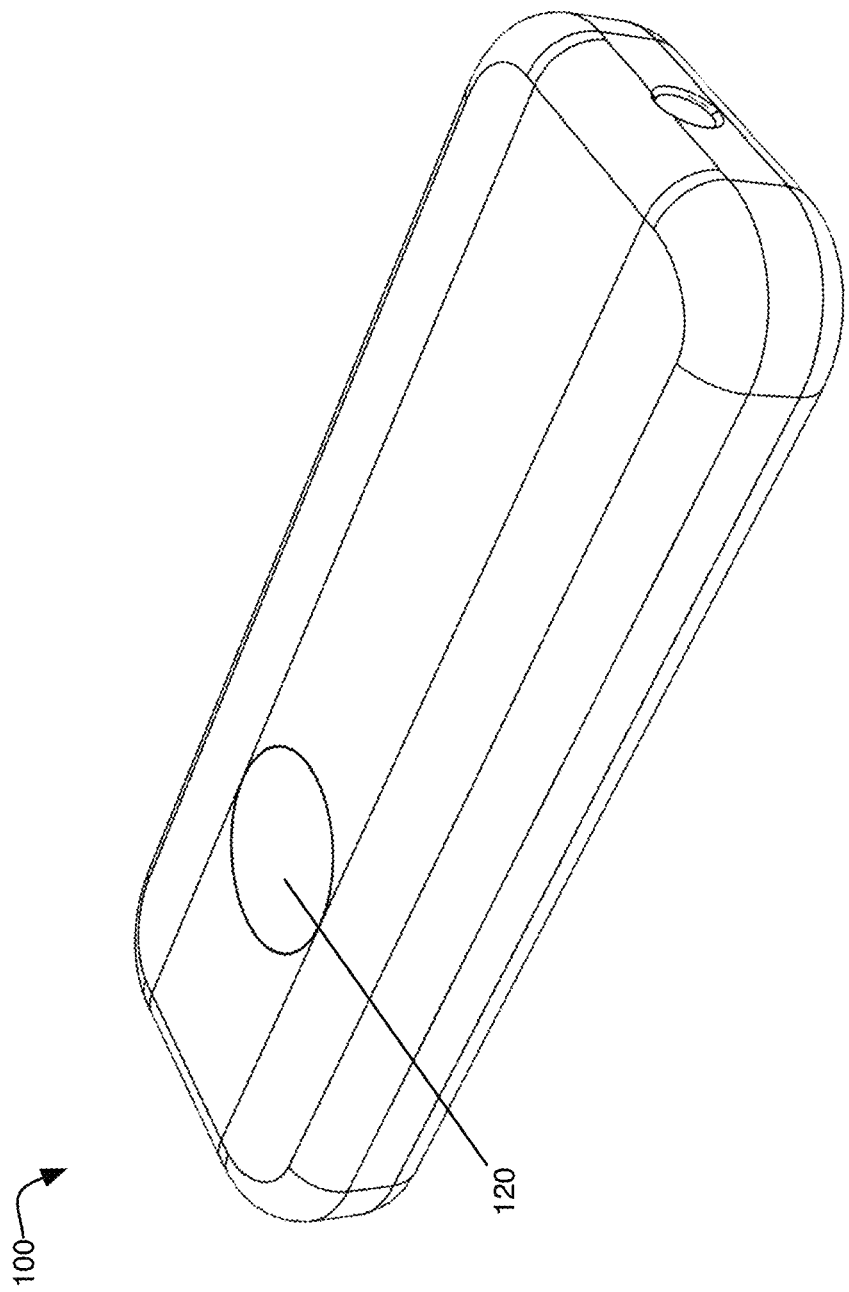
FIG. 2 is a rear perspective view of a wireless cardiac sensor.

FIG. 2 is a rear perspective view of wireless cardiac transducer 100. A rear portion of housing 105 includes button 120. Button 120 may be actuated by a user in order to initiate signal measurement by transducers 140 (FIG. 4, described further below). By placing button 120 on a surface of housing 105 that is opposite electrodes 110 and audio sensor 112, and positioned on that opposing surface at a location that is approximately centered over sensors 110 and 112, force applied by a user pressing button 120 during a measurement serves to press electrodes 110 and sensor 112 directly against the user's skin, thereby improving quality of contact with the user's skin. This configuration may be particularly helpful for applications in which a person is using wireless cardiac sensor 100 on themselves, in a one-handed mode of operation.

Figure 3:
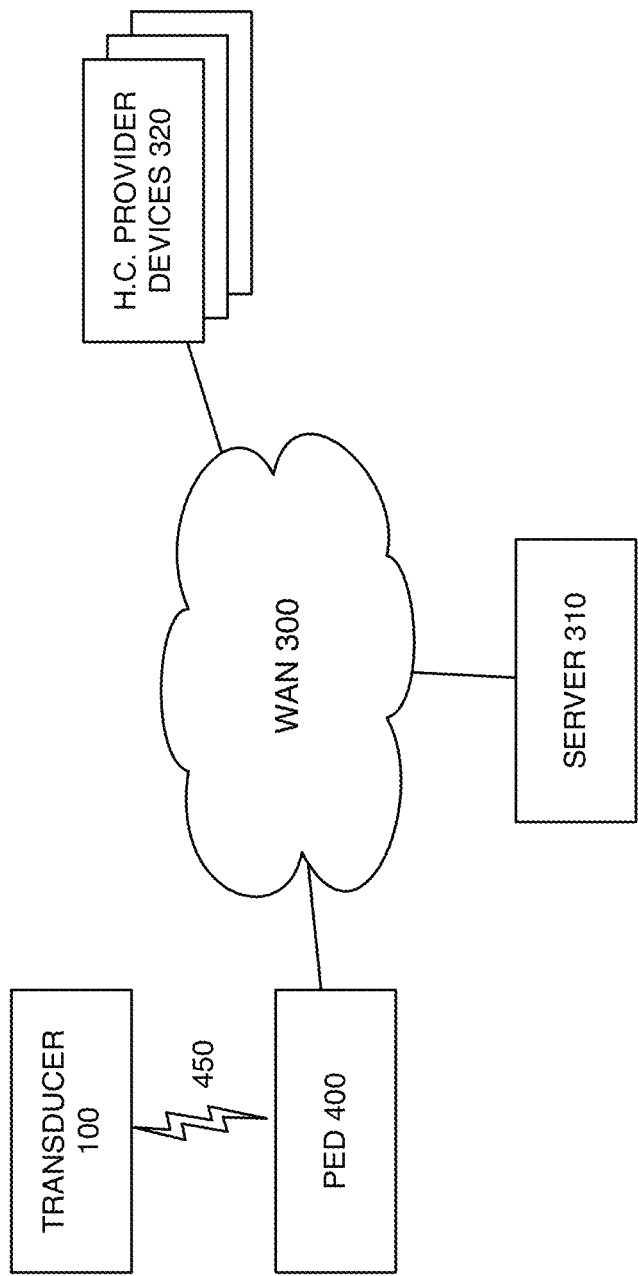
FIG. 3 is a schematic block diagram of a wireless cardiac sensor computing environment.

FIG. 3 is a schematic block diagram of an environment in which wireless cardiac transducer 100 may be beneficially employed. Transducer 100 communications with personal electronic device ("PED") 400 via wireless communications link 450, as described further hereinbelow. In some applications, PED 400 may be a computing device having diverse functionality and used for multiple purposes, such as a smartphone, tablet computer, smart watch, laptop computer, desktop computer, voice-controlled home assistant or the like. By integrating functionality between transducer 100 and PED 400, PED 400 can be used to implement various elements of functionality that are beneficial to use of transducer 100, thereby reducing the cost and complexity of transducer 100. For example, in some embodiments, PED 400 may be a smartphone having a graphical display, touchscreen and application software enabling exchange of data and control signaling with transducer 100.

PED 400 communicates with other systems and devices via wide area network (WAN) 300, which may include the Internet. In some embodiments, server 310 may be provided to implement services associated with transducer 100, such as data storage, data analysis, data publication, as well as web applications and/or application programming interfaces for same. Health care provider devices 320 are electronic systems and devices used by health care service providers, in order to exchange information with server 310 and/or PED 400, as described further hereinbelow. Devices 320 may include smartphones, tablet computers, personal computers, or healthcare service provider computing systems or equipment.

FIG. 4 is a detailed schematic block diagram of cardiac sensor 100, as it interacts with PED 400. Cardiac sensor 100 includes microprocessor 130 and digital memory 132. Battery 134 is a rechargeable battery serving to power wireless transducer 100 during operation. In some embodiments, it may be desirable for battery 134 to incorporate wireless charging circuitry, thereby enabling further minimization or avoidance of ports and other apertures within the cardiac sensor housing.

Transducer package 140 include audio transducer 142. Audio transducer 142 includes piezoelectric sensor 112; an analog-to-digital converter to digitize audio signals detected by sensor 112; as well as signal processing circuitry to filter and condition detected signals. Audio signal processing circuitry may be implemented in the analog domain (i.e. prior to digitization), in the digital domain (i.e. by microprocessor 130 and/or a dedicated digital signal processing integrated circuit) or both.

Transducer package 140 also includes ECG transducer 144. ECG transducer 144 includes ECG electrodes 110A and 110B; an analog-to-digital converter to digitize voltage differentials measured by electrodes 110A and 110B; as well as signal processing circuitry to filter and conditions detected signals. ECG signal processing circuitry may be implemented in the analog domain (i.e. prior to digitization), in the digital domain (i.e. by microprocessor 130 and/or a dedicated digital signal processing integrated circuit) or both.

Cardiac sensor wireless transceiver 136 is preferably a Bluetooth transceiver, enabling wireless digital communications with other Bluetooth-enabled devices, such as PED 400, via wireless communication link 450. In some embodiments, PED 400 may be a standard, commodity mobile wireless computing device, such as a smartphone (e.g. Apple iPhone™), tablet computer (e.g. Apple iPad™), or laptop computer. In other embodiments, PED 400 may less preferably be a dedicated computing device, such as a central sensor monitoring station with embedded software. PED 400 includes wireless (e.g. Bluetooth) transceiver 402, microprocessor 404, user interface components 406 (such as a touch-sensitive display screen, or combinations of graphical display, keyboard, mouse, touchpad or the like), digital memory 408 for data storage, and battery 410 for cordless operation. Various wireless communication protocols may be utilized to convey data between cardiac sensor 100 and PED 400, including, without limitation, those described in applicant's co-pending U.S. patent application Ser. No. 15/384,506, filed on Dec. 20, 2016, the contents of which are hereby incorporated by reference in their entirety.

By providing a cardiac sensor 100 which is compact in size, while leveraging a user's existing personal electronic device 400 for functions such as data storage, analysis, transmission and user interaction, cardiac sensor 100 may be relatively inexpensive as compared to alternative solutions.

Figure 5:
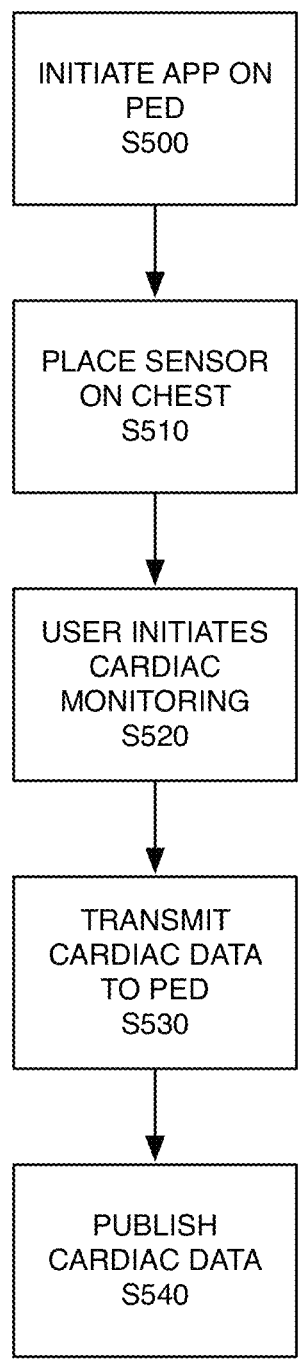
FIG. 5 is a process for using a wireless cardiac sensor.

FIG. 5 illustrates an exemplary process for using cardiac sensor 100. In step S500, a user initiates use of a software application installed on PED 400. For example, in an embodiment in which PED 400 is a smartphone, a smartphone app may be downloaded and installed on PED 400. The app may subsequently be executed by processor 404 to control operation of PED 400. When launched, the app may provide guidance and instructions to the user via UI 406. For example, the app may provide visual displays on a display screen to illustrate proper placement of cardiac sensor 100 on the user's body.

In step S510, a user places cardiac sensor 100 into contact with their chest, preferably over their left pectoral area and with guidance displayed on PED UI 406. Electrodes 110A and 110B contact the user's chest, enabling ECG transducer 144 to measure electrical changes on the skin occurring as a result of the heart muscle's electrophysiologic pattern of depolarization during each heartbeat. Simultaneously, piezoelectric sensor 112 makes physical contact with the user's chest to detect heart sounds conducted through the user's chest wall to audio transducer 142.

In step S520, the user presses button 120 to initiate cardiac monitoring. Specifically, depression of button 120 initiates simultaneous recording of ECG and heart sound data by transducer package 140. With a cardiac sensor embodiment such as that of FIGS. 1 and 2, a user may readily hold sensor 100 against their own chest with one hand, while utilizing one finger to press button 120.

In step S530, cardiac sensor 100 captures cardiac data generated by transducers 140 and transmits that data to PED 400. In the course of doing so, electrical signals generated by transducers 142 and 144 are digitized using analog-to-digital converters. Various filters and other signal processing operations may be performed on the sensed ECG and heart sound signals, either locally within cardiac sensor 100, remotely by PED 400, or elsewhere. Data may be stored for a period of time locally within cardiac sensor memory 132, before, during and/or after transmission to PED 400. Preferably, ECG and heart sound data is streamed in near-real time from sensor 100 to PED 400 via wireless communication link 450. Such cardiac data is then stored locally within PED 400 by digital memory 408.

In step S540, cardiac data received by PED 400 may be published to other stakeholders in a user's care. For example, in some embodiments, PED 400 (under control of the application initiated in step S500) may transmit recorded cardiac data to a centralized server 310 via WAN 300. Server 310 may then make the recorded cardiac data available to other services, such as health care provider computing devices 320 accessing server 310 via a web application or application programming interface. In such a use case, a patient using cardiac monitor 100 at home or in another non-clinical environment, may make data from cardiac sensor 100 available to doctors or other health care professionals in remote locations for expert diagnostic purposes.

In some embodiments, cardiac data may be streamed from sensor 100 to PED 400 to server 310, such that the data may be made available to third parties in near-real time. In some embodiments, data from cardiac monitoring sessions may be stored over time within server 310, providing a repository of historical data for subsequent analysis by, e.g., health care professionals.

In some embodiments, PED 400 may also retain a repository of historical cardiac monitoring data, with local software applications operating on PED 400 providing tools for analyzing such data and providing diagnostic results based thereon, delivered via displays on UI 406.

Figure 7:
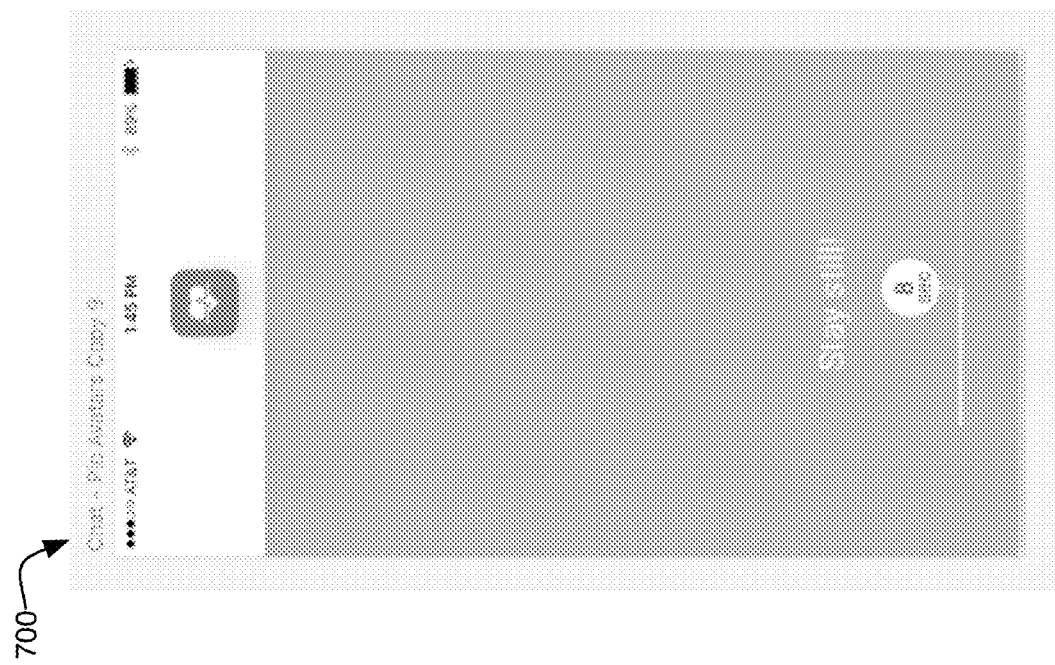
FIG. 7 is an instructional user interface display on a personal electronic device.
Figure 6:
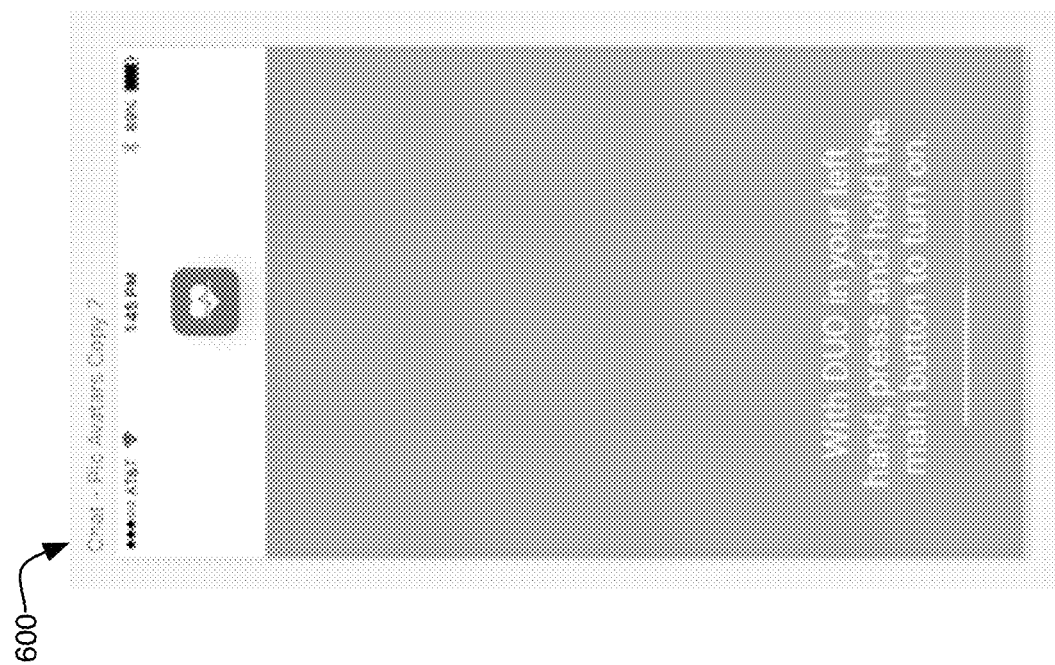
FIG. 6 is an instructional user interface display on a personal electronic device.

In some embodiments, the PED 400 may provide feedback to the user on the quality of the ECG and PCG (phonocardiogram) signals obtained, preferably including a voice-based audio feedback system to communicate this information to the user during the process of signal acquisition. In particular, PED 400 may execute a local application on microprocessor 404, to assess sensor data received via transceiver 402 and, based on that assessment, workflow logic and/or other logic implemented by the local application, provide feedback to the user via user interface 406, preferably including audio instructions and feedback via an audio loudspeaker within UI 406. For example, upon initiating a cardiac monitoring session, PED 400 may render user interface display 600 (FIG. 6) on a display screen to prompt the user regarding positioning of sensor 100, while simultaneously playing audio instructions as well. After the user presses a button to start measurement, PED 400 may render user interface display 700 (FIG. 7) on the PED display screen to instruct the user to remain still during the measurement. The audio and/or visual feedback will alert the user when a data capture is complete or when data quality is poor.

Figure 8:
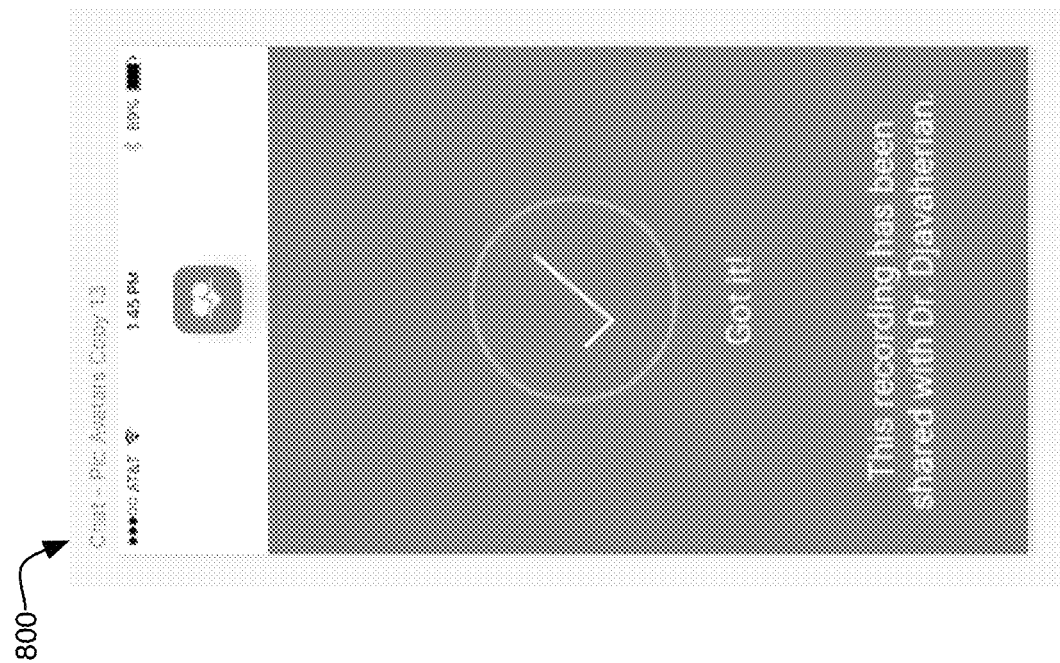
FIG. 8 is an informational user interface display on a personal electronic device.

In some embodiments, PED 400 will alert the user when a data capture is reviewed by a physician or clinician and/or is sent to the physician or clinician (such as via transmission from PED 400 to healthcare provider device 320 via wide area network 300). In particular, PED 400 may render user interface 800 (FIG. 8) to confirm transmission of sensor data to a health care provider.

Figure 9:
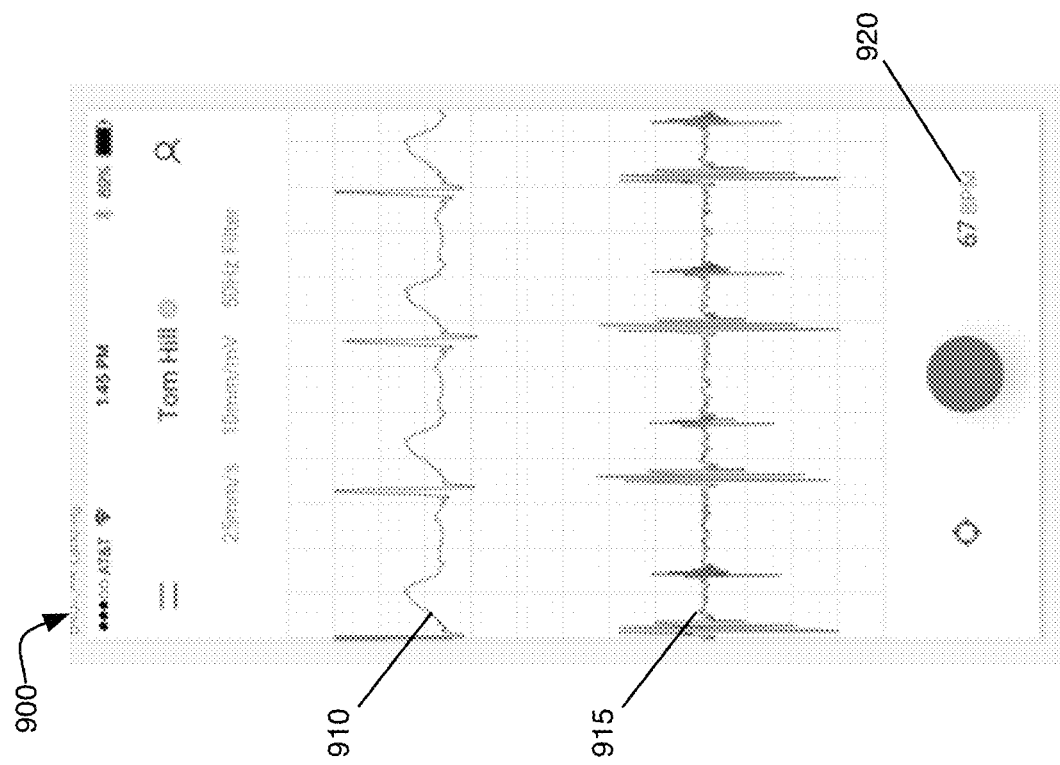
FIG. 9 is a user interface display of acquired sensor data on a personal electronic device.

PED 400 may also operate to display data acquired via sensor 100 for user review. FIG. 9 illustrates a user interface display 900 that may be rendered on a display screen. Display 900 includes two continuous waveforms 910 and 915 of the ECG and PCG data, allowing a user to compare differences or similarities between the data. Display 900 includes other diagnostic as well, derived from waveforms 910 and 915, such as heart rate output 920.

The foregoing description of the disclosed embodiments is provided to enable any person skilled in the art to make or use the invention disclosed herein. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein. All references cited herein are expressly incorporated by reference.

What is claimed is:

1. A wireless cardiac sensor comprising:
   a sensor housing having a first side for positioning against a user's chest;
   a battery within the sensor housing for powering the sensor;
   an ECG transducer within the sensor housing, the ECG transducer comprising plurality of electrodes exposed on the first side of the sensor housing for recordation of ECG data measured from skin of a patient;
   an audio transducer within the sensor housing, the audio transducer comprising an audio transducer sensor exposed on the first side of the sensor housing for recordation of heart sound data, wherein the ECG transducer comprises two electrodes positioned on opposite sides of, and adjacent to, the audio transducer sensor, such that the ECG transducer electrodes and audio transducer sensor form a sensor package occupying only a portion of the first side of the sensor housing, wherein the audio transducer sensor is circular and wherein the two electrodes each have an edge extending across a diameter of the transducer, the edge adjacent the circular audio transducer and each have linear edges defining opposite edges from the edge adjacent the circular audio transducer; and a wireless transceiver, the transceiver adapted for transmitting said ECG data recorded by the ECG transducer and said heart sound data recorded by the audio transducer, to a personal electronic device proximate the sensor.

2. The sensor of claim 1, in which the sensor housing is approximately rectangular cuboid in shape having longer rounded edges and shorter rounded edges, and wherein the opposite edges of the two electrodes are aligned with the shorter rounded edges of the housing.

3. The sensor of claim 2, wherein the sensor housing also has a second side opposite the first side, the sensor further comprising a button for actuation by a user, the button exposed on the second side of the sensor housing and positioned directly above the sensor package, the second button being circular but being smaller than the circular audio transducer housing.

4. The cardiac sensor of claim 1, further comprising the personal electronic device proximate the cardiac sensor ("PED"), the PED comprising:
a PED wireless transceiver configured for communication with the sensor wireless transceiver to convey the cardiac data therebetween; and
a user interface comprising a graphical display screen configure to render displays conveying diagnostic information received by the PED wireless transceiver.

5. The sensor of claim 1, wherein the housing is a generally rectangular cuboid in shape, with rounded edges, and wherein the first side is generally rectangular with the two electrodes and audio transducer sensor positioned on one end of the first side, wherein each of the two electrodes and audio transducer sensor extend fully from a first rounded edge to a second opposite rounded edge of the housing.

6. The sensor of claim 5, wherein each ECG electrode has three linear sides such that together, the ECG electrodes and the audio transducer sensor form and fill a rectangular shape with curved edges.

7. A wireless cardiac sensor comprising:
a sensor housing having a first rectangular side for positioning against a user's chest, wherein the sensor housing is a rectangular cuboid in shape having first and second long rounded edges and first and second short rounded edges;
a battery within the sensor housing for powering the sensor;
an ECG transducer within the sensor housing, the ECG transducer comprising plurality of electrodes exposed on a first side of the sensor housing for recordation of ECG data measured from skin of a patient;
an audio transducer within the sensor housing, the audio transducer comprising an audio transducer sensor exposed on the first side of the sensor housing for recordation of heart sound data, wherein the ECG transducer electrodes and the audio transducer sensor collectively form a sensor package on the first side of the sensor housing, wherein a first ECG transducer has a first curved and linear edge at the first short rounded edge and a second transducer has a first curved and linear edge positioned away from the second short rounded edge, and wherein the first curved and linear edges of the first and second transducer extend across the diameter of the audio transducer; and
a wireless transceiver, the transceiver adapted for transmitting said ECG data recorded by the ECG transducer and said heart sound data recorded by the audio transducer, to a personal electronic device in near-real time;
in which the sensor housing also has a second side opposite the first side, the sensor further comprising a button for actuation by a user, the button exposed on the second side of the sensor housing and positioned directly above the sensor package.

8. The cardiac sensor of claim 7, wherein the button is centered over the sensor package, whereby application of pressure on the button by a user holding the sensor against the user's chest promotes contact of the sensor with the user's chest.

9. A wireless system, comprising:
a sensor housing having a first side for positioning against a user's chest;
a battery within the sensor housing for powering the sensor;
an ECG transducer within the sensor housing, the ECG transducer comprising plurality of electrodes exposed on the first side of the sensor housing for recordation of ECG data measured from skin of a patient;
an audio transducer within the sensor housing, the audio transducer comprising an audio transducer sensor exposed on the first side of the sensor housing for recordation of heart sound data,
wherein the ECG transducer comprises two electrodes positioned on opposite sides of, and adjacent to, the audio transducer sensor, such that the ECG transducer electrodes and audio transducer sensor form a sensor package occupying only a portion of the first side of the sensor housing, wherein the audio transducer sensor is circular and wherein the two electrodes each have an edge extending across a diameter of the transducer, the edge adjacent the circular audio transducer and each have linear edges defining opposite edges from the adjacent edges;
a wireless transceiver, the transceiver adapted for transmitting said ECG data recorded by the ECG transducer and said heart sound data recorded by the audio transducer, to a personal electronic device proximate the sensor; and
the personal electronic device proximate the sensor ("PED"), the PED comprising:
a PED wireless transceiver configured for communication with the sensor wireless transceiver to convey cardiac data therebetween; and
a user interface comprising a graphical display screen configure to render displays conveying diagnostic information derived from cardiac data received by the PED wireless transceiver, wherein the user interface is configured to visually prompt the user regarding positioning of the housing.

10. The system of claim 9, wherein the user interface is further configured to simultaneously play audio instructions while prompting the user regarding positioning.

11. The system of claim 10, wherein the user interface is further configured to, after the user presses a button, the button exposed on the second side of the sensor housing and positioned directly above the sensor package, to start measurement, instruct the user to remain still during the measurement.

12. The system of claim 10, wherein the user interface is further configured to alert the user when a data capture is reviewed by a physician or clinician.

13. The system of claim 10, wherein the user interface is further configured to alert the user when a data capture is sent to a physician or clinician.

* * * * *